United States Patent
Sibai

(10) Patent No.: US 12,076,282 B2
(45) Date of Patent: *Sep. 3, 2024

(54) DRAIN TRAY ASSEMBLY, SYSTEM AND METHOD

(71) Applicant: SURGICAL SERVICES & SOLUTIONS LLC, Bloomington, IN (US)

(72) Inventor: Tarek Sibai, Bloomington, IN (US)

(73) Assignee: SURGICAL SERVICES & SOLUTIONS LLC, Bloomington, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/950,190

(22) Filed: Sep. 22, 2022

(65) Prior Publication Data

US 2023/0018437 A1   Jan. 19, 2023

Related U.S. Application Data

(63) Continuation of application No. 16/659,184, filed on Oct. 21, 2019, now Pat. No. 11,471,355.

(60) Provisional application No. 62/747,975, filed on Oct. 19, 2018.

(51) Int. Cl.
*A61G 13/10* (2006.01)
*A61M 1/00* (2006.01)

(52) U.S. Cl.
CPC .............. *A61G 13/102* (2013.01); *A61M 1/60* (2021.05); *A61M 1/71* (2021.05); *A61M 1/741* (2021.05); *A61M 1/64* (2021.05); *A61M 1/882* (2021.05)

(58) Field of Classification Search
CPC ......... A61G 13/102; A61M 1/60; A61M 1/71; A61M 1/741; A61M 1/64; A61M 1/882; A61M 1/69

See application file for complete search history.

(56) References Cited

U.S. PATENT DOCUMENTS

| | | | |
|---|---|---|---|
| 4,082,257 A | 4/1978 | Strickland | |
| 4,243,214 A | 1/1981 | LaRooka | |
| 4,947,418 A * | 8/1990 | Barr | A61G 1/00 5/607 |
| 5,349,965 A | 9/1994 | McCarver | |
| 5,655,258 A * | 8/1997 | Heintz | A61G 13/102 604/317 |

(Continued)

FOREIGN PATENT DOCUMENTS

WO   WO-2007030103 A1 *   3/2007   ........... A61G 13/102

*Primary Examiner* — Susan S Su
*Assistant Examiner* — Eric Rassavong
(74) *Attorney, Agent, or Firm* — Brannon Sowers & Cracraft PC

(57) ABSTRACT

A surgical drain tray assembly includes a fluid impermeable first layer and a porous second layer positioned on the fluid impermeable first layer. The fluid impermeable first layer includes a drain outlet, a basin, and a sloping surface angled toward the basin, the drain outlet being positioned within the basin. The porous second layer may be formed of a foam material and includes a top work surface. Fluids spilled onto the work surface pass through the porous second layer to the fluid impermeable first layer. The sloping surface of the fluid impermeable first layer conveys the fluids toward the basin for draining through the drainage outlet.

20 Claims, 8 Drawing Sheets

(56) References Cited

U.S. PATENT DOCUMENTS

| | | | |
|---|---|---|---|
| 6,077,221 A * | 6/2000 | Fowler, Jr. | A61B 17/0293 |
| | | | 600/233 |
| 6,102,073 A | 8/2000 | Williams | |
| 6,387,379 B1 | 5/2002 | Goldberg | |
| 7,131,965 B1 | 11/2006 | Thornbury et al. | |
| 7,291,376 B1 * | 11/2007 | Siegel | A47L 23/266 |
| | | | 428/167 |
| 9,320,668 B1 * | 4/2016 | Born | A61G 13/1205 |
| 9,693,930 B2 * | 7/2017 | Gathers | A47K 1/04 |
| 2003/0056285 A1 * | 3/2003 | Pollastri | A61G 13/102 |
| | | | 4/574.1 |
| 2007/0251855 A1 * | 11/2007 | Curnow | A61B 50/33 |
| | | | 206/586 |
| 2008/0306457 A1 * | 12/2008 | Ryan | A61M 1/84 |
| | | | 604/317 |
| 2008/0306458 A1 | 12/2008 | Chandrasekar et al. | |
| 2011/0011408 A1 * | 1/2011 | Born | A61B 50/33 |
| | | | 128/845 |
| 2012/0325704 A1 | 12/2012 | Kerns | |
| 2014/0283925 A1 * | 9/2014 | Justus | A61M 1/79 |
| | | | 137/312 |
| 2014/0352699 A1 | 12/2014 | Bom | |
| 2016/0199242 A1 * | 7/2016 | Born | A61G 13/102 |
| | | | 128/845 |
| 2017/0281446 A1 | 10/2017 | Parsell | |
| 2019/0175432 A1 * | 6/2019 | Stephens | A61G 7/0503 |
| 2022/0079827 A1 * | 3/2022 | Lombardo | A61G 13/102 |

\* cited by examiner

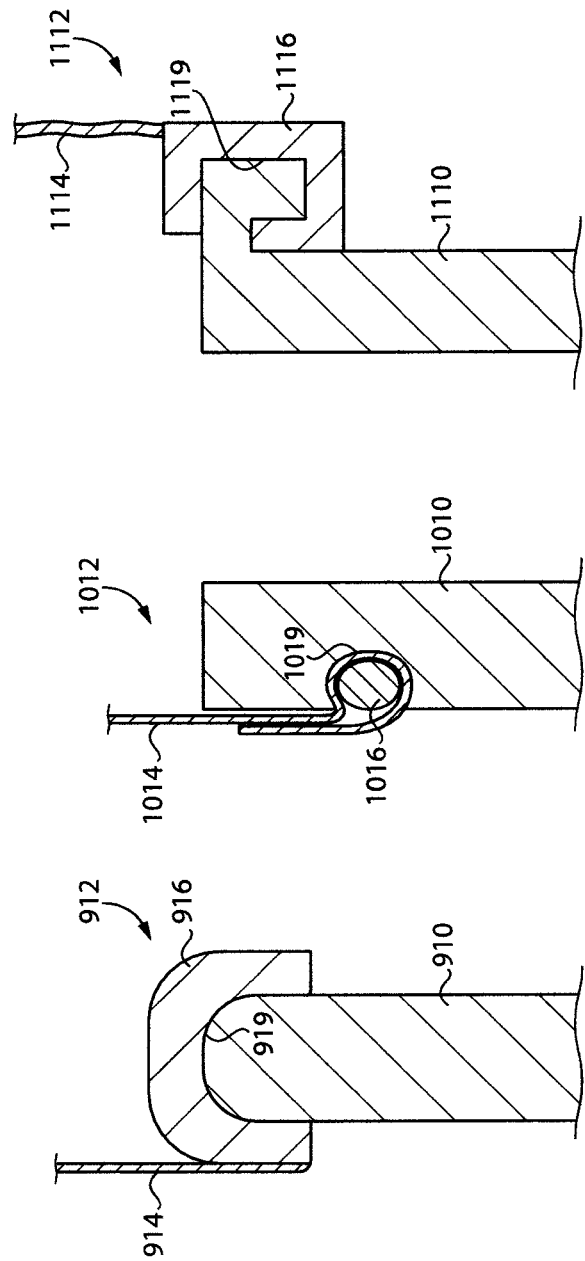

DRAIN TRAY ASSEMBLY, SYSTEM AND METHOD

CROSS-REFERENCE TO RELATED APPLICATIONS

The present disclosure is a continuation of U.S. patent application Ser. No. 16/659,184, filed Oct. 21, 2019, which claims priority under 35 U.S.C. § 119(e) to U.S. Provisional Patent Application No. 62/747,975 filed on Oct. 19, 2018, all of which are expressly incorporated by reference herein.

TECHNICAL FIELD

The present disclosure relates generally to apparatus for use in medical procedures and, more particularly, to devices for draining and/or collecting fluids during a medical procedure.

BACKGROUND

When irrigating limbs or other body parts in a surgical or non-surgical setting such in an emergency room or other clinic setting, in many circumstances medical providers find the need to irrigate potentially contaminated areas before, during, and/or after procedures to keep the wound hydrated, assist with visualization, and remove debris, bodily fluids, contaminants, purulent materials or tissue and the like from the site. By design, the irrigation fluid or irrigant will spill out of the working site, and on to surrounding surfaces, providers, patients, and, ultimately, the floor. The overflowing fluids typically contain bodily fluids from the patient along with other infectious or potentially harmful particles and/or fluids. Suction tube devices or non-conforming containers are used to collect as much of the overflowing fluid as possible, but these techniques are often incapable of efficient collection of fluids and debris in a safe and expedient manner and therefore insufficient to prevent spilling. This can be especially problematic when working on a patient's limb, for instance, because the limb is typically extended flat and outward on a flat surface. As a result, overflowing fluids commonly spill onto the working table or other surfaces, surgical instruments, medical professionals, or the floor, amongst other things, which can create a hazardous situation for both the patient and hospital staff. In response, towels, sponges, and/or buckets or other non-conforming containers are often placed in the areas immediately on, adjacent to, and in dependent areas close to the working site.

There have been a number of attempts to address this issue. For instance, United States Patent Publication No. 2014/0352699 to Born ("Born") discloses a rectangular drainage platform sized and shaped to support a patient's limb during surgery. Born's device includes a planar, slotted work surface supported above a fluid pan having one or more drainage outlets. Another strategy is disclosed in U.S. Pat. No. 6,102,073 to Williams ("Williams"). Williams teaches a draining device for an operating room floor formed of a fluid impervious base having a flexible, porous mat disposed on a plurality of protuberances extending upward from the base. Williams' device further includes a fluid outlet for draining collected fluids. While these and other solutions may be useful for draining fluids in certain contexts, there remains ample room for improvement to allow for an efficient, simple, and provider friendly way to collect and drain fluids during medical procedures.

SUMMARY OF THE INVENTION

In one aspect, a drain tray assembly for use during a medical procedure includes a fluid impermeable pan layer having a basin, a sloping surface angled toward the basin and oriented at a slope angle relative to a horizontal plane, and a drainage outlet within the basin. The drain tray assembly further includes a porous foam layer positioned on the fluid impermeable pan layer, and including a bottom surface, and a top work surface. The top work surface is oriented at a work surface angle relative to the horizontal plane that is less than the slope angle and equal to 0° or greater.

In another aspect, a system for draining fluids during a medical procedure includes a drain tray assembly having a fluid impermeable pan with a basin, a sloping surface forming a flow path in the direction of the basin, a drainage outlet within the basin, and a porous foam laying having a top work surface, and a bottom surface supported upon the fluid impermeable pan. The top work surface has an orientation, relative to a horizontal plane, that ranges from parallel to the horizontal plane to parallel to the sloping surface. The porous foam layer is structured to pass fluids from the top work surface to the sloping surface of the fluid impermeable pan, and the sloping surface of the fluid impermeable pan is structured to convey fluids to the basin under the force of gravity for draining through the drain outlet.

In still another aspect, a method of draining fluids during a medical procedure includes receiving fluids on a porous work surface formed on a layer of foam material of a drain tray assembly, passing the fluids from the porous work surface through the layer of foam material toward a layer of a fluid impermeable material of a drain tray of the drain tray assembly. The method still further includes conveying the fluids under the force of gravity toward a drainage outlet of the drain tray by way of a sloping surface of the layer of the fluid impermeable material of the drain tray, and draining the fluids out of the drain tray by way of the drainage outlet.

BRIEF DESCRIPTION OF THE DRAWINGS

FIG. 23 is a sectioned view of a fastening arrangement for a drain tray and drape, according to one embodiment;

FIG. 24 is a sectioned view of a fastening arrangement for a drain tray and drape according to one embodiment;

FIG. 25 is a sectioned view of a fastening arrangement for a drain dray and drape, according to one embodiment.

DETAILED DESCRIPTION

Figure 1:
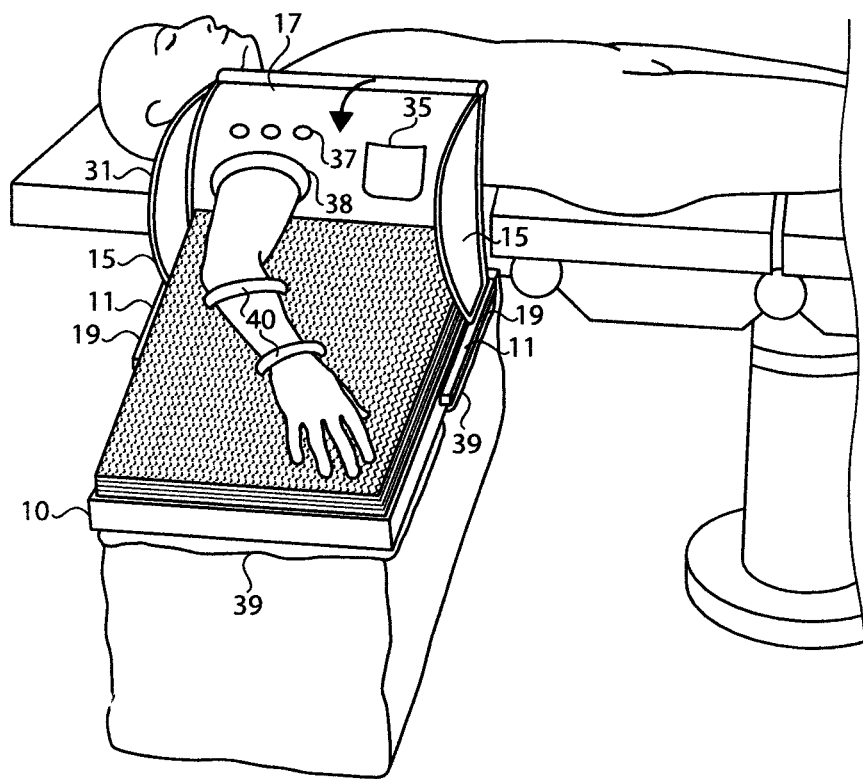
FIG. 1 is a diagrammatic perspective view of a drain tray assembly and system for use during a medical procedure, according to one embodiment.

Referring now to FIG. 1, a perspective view of a drain tray or drain tray assembly ("tray") 10 for draining irrigant and other fluids (hereinafter, "fluids") spilled out or otherwise flowing from a working site during a medical procedure is shown according to one embodiment. FIG. 1 shows how tray 10 might be deployed in an operating room, emergency room, or clinical setting. Tray 10 of the present embodiment is structured to be used when performing a medical procedure on a patient's arm, although embodiments are contemplated in which tray 10 is structured to be used for medical procedures involving other limbs or even for medical procedures involving a patient's head, neck, or torso. Tray 10 might be structured to rest upon a projection or other surface of a procedure table, and might also include additional features to adhere to the operating table or to otherwise remain in place during a procedure, such as clips, bolts, Velcro®, straps, or adhesives (not shown). These and other features of tray 10 discussed herein may allow tray 10 to be deployed without requiring installation of additional equipment or modification of existing equipment in many instances.

Figure 2:
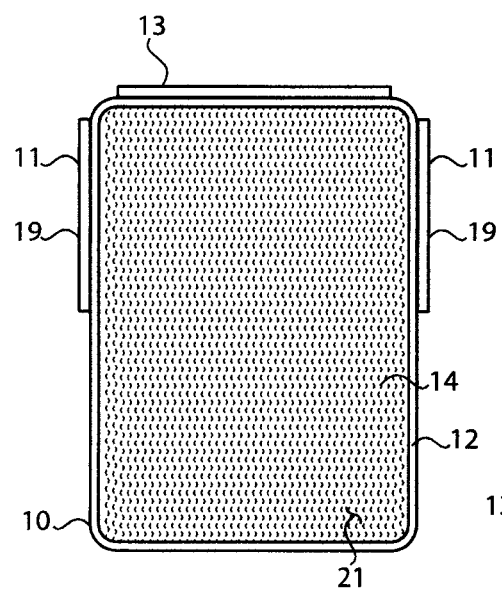
FIG. 2 is a diagrammatic top view of a drain tray assembly, according to one embodiment.
Figure 3:
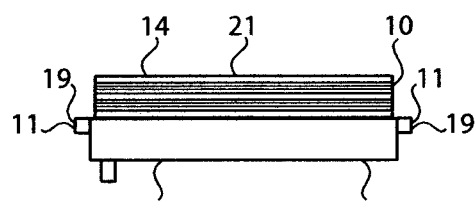
FIG. 3 is a diagrammatic front view of a drain tray assembly, according to one embodiment.
Figure 4:
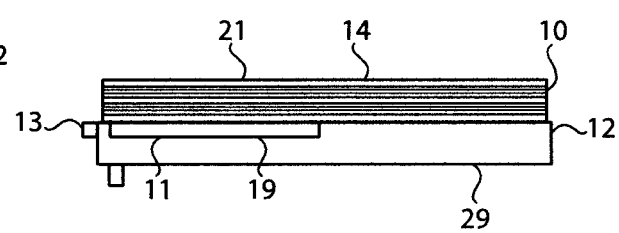
FIG. 4 is a diagrammatic side view of a drain tray assembly, according to one embodiment.
Figure 14:
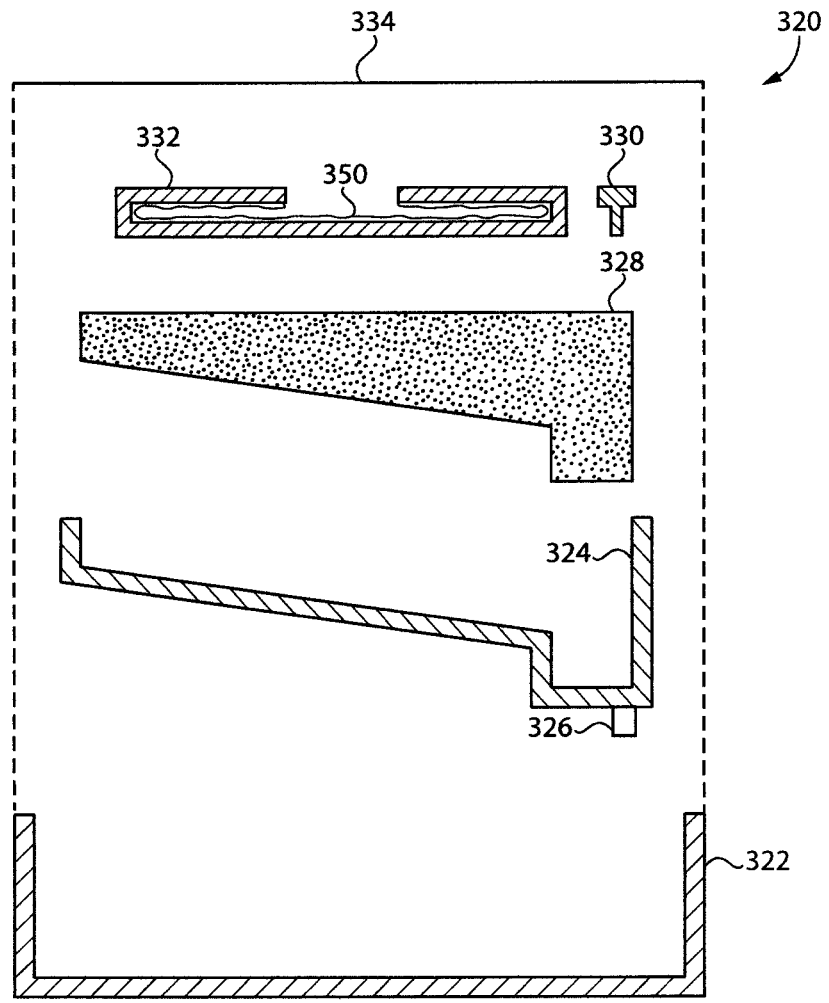
FIG. 14 is a partially sectioned, exploded side view of sterile packaging containing a drain tray assembly, according to one embodiment.

Tray 10 might include one or more curtain assemblies 11 each having a curtain 15 and a curtain attachment 19 coupling curtain 15 with tray 10. Curtain assemblies 11 may further include a frame 31 structured to allow curtain 15 to form a shield between tray 10 and the medical staff and/or floor. Frame 31 may be elastically deformable such as for packaging or adjustment during service. Curtain 15 may be a retractable or collapsible or can be adjustably extended (such as by unrolling from the end closest to the patient) or collapsed from or on sliding on curtain attachment 19. In some embodiments, curtain 15 might be attached directly to at least one of a fluid impermeable first layer 12 or a porous second layer 14 of tray 10 (as shown in FIGS. 2-4, discussed hereinafter) by way of adhesives, Velcro®, or other fastening mechanisms. Attachments of a curtain or drape in a drain tray assembly as contemplated herein could be by way of any suitable mechanism, including adhesives, Velcro®, tape, clips, clamps, magnets, or still others. Further, curtain attachment 19 may be slidable or otherwise adjustable relative to tray 10, or could have a range of lengths different from what is illustrated. In other embodiments, curtain assembly 11 or the fluid impermeable layer 12 or the fluid permeable layer 14 might be structured to provide an attachment means for a commercially available or otherwise suitable curtain. Curtain 15 may be attached inside walls of tray 10, or externally. An internal biaser such as an elastic band can be provided to bias curtain 15 to a collapsed or rolled-up configuration. An example elastic band 350 is shown in FIG. 14, discussed hereinafter.

Tray 10 can also include a drape attachment 13 (not shown in FIG. 1) coupling a drape 17 therewith. Drape 17 can be configured to fit around a patient's limb by, for example, using an adhesive 38—for instance, medical tape or the like—to adhere drape 17 to the patient. In some embodiments, drape 17 might instead be structured to receive and/or fit elastically around a patient's limb. For instance, drape 17 could include an elastic sleeve attachment. Drape 17 can also include a pouch 35 that can be used to store medical instruments or any other objects, and one or more ports 37 structured to receive medical tubing, electric cords, or the like (not pictured). In other embodiments, drape attachment 13 may be structured to attach any other commercially available or otherwise suitable drape 17. Drapes (not numbered) may also be provided to hang from tray 10, and tray 10 might include one or more cords or straps 39 to cinch drapes underneath tray 10 to allow access to foot-controlled devices and instruments and prevent accessory and redundant drapes from intruding upon the medical staff's foot and leg areas. Drapes and curtains, and potentially a frame supporting them may also be structured to be movable between a deployed configuration (FIG. 1) and a collapsed or folded configuration. Drape 17 and curtains 15 can act as a sterile barrier between tray 10 and a non-sterile table such that substantially all surfaces of the table are covered or protected. In other embodiments, tray 10 could be supported upon a table or other structure separate from the operating table, and could include drapes or a similar covering that might include one or more pouches or pockets. As discussed herein, the terms "drape" and "curtain" are used for convenience, and discussion of one of drapes or curtains can be understood to refer to the other. Tray 10 may also include one or more cords or straps 40 for immobilizing the patient's limbs, hands, digits, head, torso, or the like.

Figure 9:
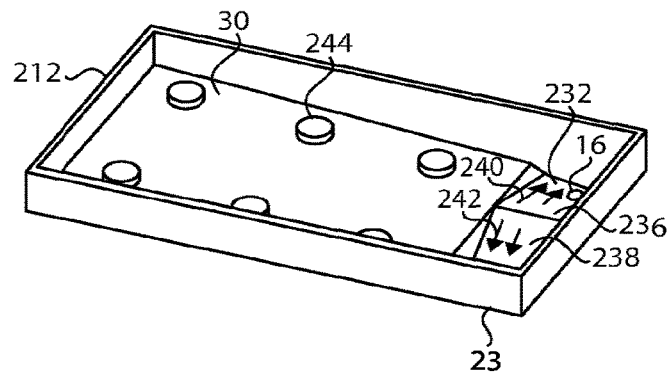
FIG. 9 is a diagrammatic perspective view of a drain tray, according to still another embodiment.

Referring now also to FIGS. 2-4, top, front, and side views of tray 10 are shown, respectively. Tray 10 includes fluid impermeable first layer 12 and porous second layer 14 upon fluid impermeable first layer 12. Porous second layer 14 includes a substantially planar horizontally oriented work surface 21, and can be formed of a fluid resistant and/or hydrophobic foam material or analogous type of material suitable for use in the medical context, and that is relatively rigid and structured to resist fluid absorption. In this way, porous second layer 14 may be capable of supporting a patient's limb without experiencing undue deformation, while allowing fluids to pass from work surface 21 to fluid impermeable first layer 12 without being unduly absorbed by the foam material, although porous second layer 14 will not be rigid to the point of producing undue pressure on the patient's limb or other body part to prevent skin pressure injuries or nerve compression problems. Porous second layer 14 will typically be less rigid than fluid impermeable first layer 12. Porous second layer 14 may include a foam block (hereinafter "foam block 14"), that may be shaped so as to mate with fluid impermeable first layer 12. Foam block 14 could also be pre-formed to be complementary to parts of a patient's body it supports. The foam material may be relatively inexpensive as foam block 14 may be disposed of after a single use, although embodiments in which foam block 14 could be reused are also contemplated. The foam material may be an open-cell foam material, a foam material with bore holes formed therein, or any other suitable type of foam material, and might be selected based at least partially on an average, minimum, or maximum pore size such that particles spilled onto work surface 21 having a dimension equal to or greater than the pore size may come to rest on work surface 21 rather than pass through to fluid impermeable first layer 12 for draining. The foam material may include, for instance, about thirty pores per square inch. In some embodiments, the foam material might be relatively dense and/or rigid such that surgeons or other medical professionals can temporarily and safely store one or more medical instruments such as a scalpel blade or needle or sharp tool end such as a bovie tip, a drill bit, or others in foam block 14 during a procedure. By way of example, a surgeon might be able to stick the blade of a scalpel into foam block 14 to keep it close without having to leave the blade exposed, or positioned outside the surgical field. In some embodiments, straps 40 may be anchored in or to foam block 14, although embodiments in which straps 40 are attached to or coupled with fluid impermeable first layer 12 or through that layer to attach to the underlying tray 10 are also contemplated. The foam material may be heparinized to prevent blood from coagulating during procedures. Embodiments in which the foam material additionally or alternatively includes other chemicals, compounds, or medications—for example, lubricants, emollients, other anticoagulants, lubricating or hydrophilic coating, antiseptics, antibacterials, or antifungals—are also contemplated. Foam block 14 in part or in full may be removable from tray 10 such that fluid impermeable first layer 12 can be used in isolation. In some embodiments, fluid impermeable first layer 12 may include pegs, studs, or other types of protrusions 244 (as shown in the embodiment of FIG. 9, discussed hereinafter) that may grip or otherwise insert into foam block 14, although embodiments in which foam block 14 may include recesses, channels, holes, or the like to receive the protrusions upon fluid impermeable first layer 12 to prevent lateral or rotational movement of foam block 14 within tray 10 are also contemplated. In still other embodiments, foam block 14 in part or in full can be adhered to fluid impermeable first layer 12 during the manufacturing process or any time thereafter.

Figure 5A:
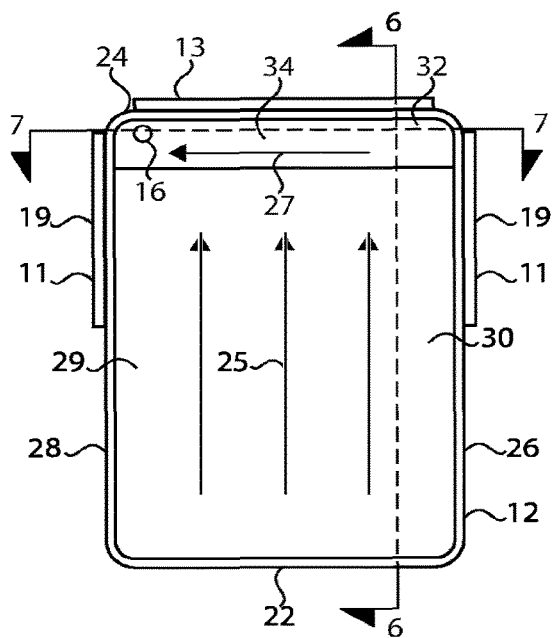
FIG. 5a is a diagrammatic top view of a drain tray, according to one embodiment.
Figure 5B:
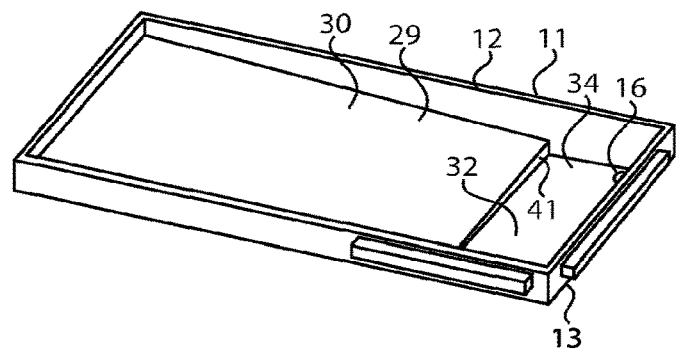
FIG. 5b is a diagrammatic perspective view of a drain tray, according to one embodiment.

Referring now also to FIGS. 5a and 5b, top and perspective views of fluid impermeable first layer 12 are shown without foam block 14. Fluid impermeable first layer 12 includes a fluid pan (hereinafter "fluid pan 12") formed of a rigid yet relatively inexpensive material, such as a plastic material suitable for use in the medical context that is molded as one-piece by injection or compression molding, thermoforming, or machined. The use of relatively inexpensive materials allows tray 10 to be disposed of after a single use, thereby eliminating or at least reducing the expense associated with removing excess fluids and with disinfecting or sterilizing equipment and other surfaces after a procedure. In other embodiments, fluid pan 12 may be formed of a durable material such as stainless steel or any other durable, reusable, sterilizable material suitable for use in the medical context such as for example polycarbonate.

Fluid pan 12 includes a front side 22, a back side 24, a right side 26, a left side 28, and a bottom side 29. The terms "right" and "left," "front" and "back," and like directional terms are used in a relative sense, each in relation to each other when viewing tray 10 or its components, and should not necessarily be taken to mean that tray 10 or its components have a particular orientation unless expressly stated or otherwise apparent from context. Fluid pan 12 also includes at least one drain outlet 16 formed within at least one of sides 22, 24, 26, 28 and/or corners formed by the intersection of sides 22, 24, 26, 28. A connector piece 23 can be attached to fluid pan 12 at drain outlet 16, and may be structured to couple drainage tubing (not pictured) with tray 10 for draining fluids from fluid pan 12 during a procedure. Drain outlet 16 and connector piece 23 can be positioned on fluid pan 12 such that any tubing attached to connector piece 23 can be positioned outside of the medical staff's work space. The drain outlet can be in a horizontal position on the sides on the tray, oriented vertically protruding from the tray, for instance. The drain outlet and connector piece may be also designed to be part of the inherent design of the tray 10 and not an adjunctive/additional component. Commercially available tubing may be attached to this outlet and/or the connector piece.

Figure 7:
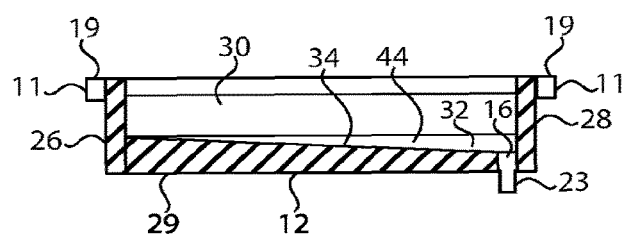
FIG. 7 is a sectioned back view of a drain tray, according to one embodiment.

Positioning of drain outlet 16 and connector piece 23 on the back-left corner of tray 10, and generally behind curtain 15, may allow operating room staff to have a wide range of unobstructed movement around the patient's limb during surgery. In other embodiments, drain outlet 16 might be within a sterile field in front of curtain 15. It can also be seen that tray 10 of the present embodiment may be manufactured to have a particular orientation in service. As such, tray 10 could be manufactured to have different orientations, and the particular configuration of tray 10 selected may be based on the particular limb or other body part being operated on. Other embodiments of the fluid pan might have multiple drainage outlets 16 (for example, fluid pan 212 as seen in FIG. 7, discussed hereinafter). In such embodiments, one or more drainage outlets 16 might be blocked during the procedure to direct a flow of fluids to a single drain outlet 16, or a drain tube could be coupled with each drain outlet 16.

Figure 6:
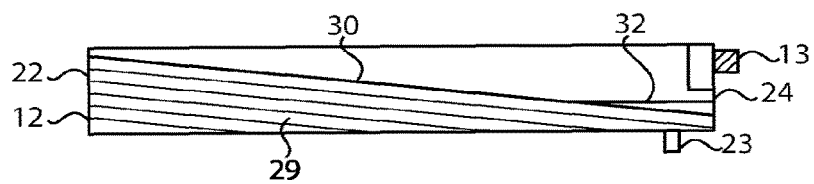
FIG. 6 is a sectioned side view of a drain tray, according to one embodiment.
Figure 12:
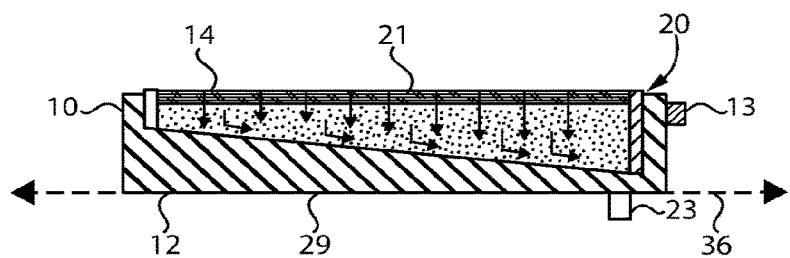
FIG. 12 is a sectioned side view of a drain tray assembly, according to one embodiment.

Bottom side 29 of fluid pan 12 includes a sloping surface 30 and a basin 32, with drainage outlet 16 being positioned on fluid pan 12 within basin 32. Sloping surface 30 may be angled relative to a horizontal plane 36 (as shown in FIG. 12, discussed hereinafter) to direct a flow of fluids under the force of gravity along a flow path 25 toward basin 32. Basin 32 may also include a sloping surface 34 that is angled relative to horizontal plane 36 for directing a flow of fluids along a flow path 27 toward drainage outlet 16. Referring now also to FIG. 6, a sectioned view of fluid pan 12 is shown at a cross-section 6-6 of FIG. 5a. FIG. 6 shows sloping surface 30 is angled to direct fluids toward back side 24, which is adjacent to basin 32. Referring now also to FIG. 7, a sectioned view of fluid pan 12 is shown at a cross-section 7-7 of FIG. 5a. FIG. 7 shows sloping surface 34 is angled to direct a flow of fluids direction toward drainage outlet 16. It will be appreciated that sloping surfaces 30, 34 may be angled differently to direct the flow of fluids in different directions where drainage outlet is not positioned on the back-left corner of fluid pan 12. Bottom side 29 may further include a surface 41 oriented substantially vertically and in opposition to at least one surface of foam block 14. For example, surface 41 of bottom side 29 in the present embodiment is substantially parallel with sides 22, 24 and may be structured to oppose lateral or side movement of foam block 14 in certain instances.

Figure 8:
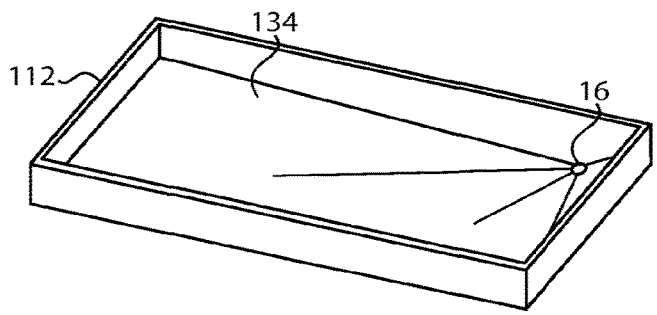
FIG. 8 is a diagrammatic perspective view of a drain tray, according to another embodiment.

Referring now to FIG. 8, a fluid pan 112 is shown according to a second embodiment. Fluid pan 112 is similar to fluid pan 12 in many respects, except that a sloping surface 134 of fluid pan 112 may not include a separate basin, instead being structured to direct a flow of fluids toward drainage outlet 16. It should be noted that material differences between embodiments will be discussed herein, and absent such discussion different embodiments should generally be understood to be alike in structure and function unless a different structure or function is apparent from the relevant context.

Referring now to FIG. 9, a fluid pan 212 is shown according to a third embodiment. Fluid pan 212 is similar to fluid pan 12 in many respects, except that fluid pan 212 may include two or more drainage outlets 16. Additionally, fluid pan 212 may have a basin 232 structured to convey fluids from sloping surface 30 to each of the two or more drainage outlets 16. Only one outlet is visible in the illustration of FIG. 9, but it will be appreciated that a second drain outlet may be positioned generally opposite the one illustrated, in the bottom corner of fluid pan 212 FIG. 9 For instance, as can be seen in FIG. 9, basin 232 has a first sloping surface 236 and a second sloping surface 238, each being structured to convey fluids to a different drainage outlet along a first flow path 240 and a second flow path 242. As can be seen when comparing the embodiments of FIGS. 8 and 9 with the embodiment of FIGS. 1-7, a height of sides 22, 24, 26, 28 may differ between embodiments. For example, sides 22, 24, 26, 28 are relatively short in the embodiment of FIGS. 1-7 as compared to the embodiments of FIGS. 8 and 9. In certain circumstances, higher sides 22, 24, 26, 28 might be desirable—for instance, if the patient's limb is or may be likely to move during surgery, which might cause foam block 14 to become dislodged from fluid pan 12 in the embodiment of FIGS. 1-7. Further, as can be seen, fluid pan 212 includes a plurality of protrusions 244 structured to engage foam block 14 so as to prevent undesirable lateral, rotational, or other movement within tray 10. As discussed above, in some embodiments, protrusions 244 may be sized, shaped, or arranged differently, or be different in number than what is illustrated. Foam block 14 might be alternatively structured to have protrusions that are received in cavities in tray 10.

Figure 10:
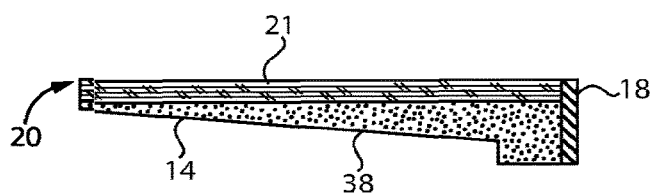
FIG. 10 is a sectioned side view of a component of a drain tray assembly, according to one embodiment.
Figure 11:
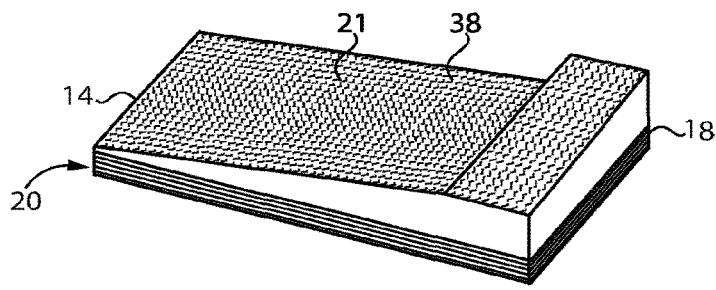
FIG. 11 is a bottom perspective view of a component of a drain tray assembly, according to one embodiment.

Referring now again to FIGS. 1-7, and now also to FIGS. 10 and 11, it can be seen that foam block 14 is structured for positioning within fluid pan 12. FIG. 10 shows a partially sectioned side view of foam block 14, and FIG. 11 shows a bottom perspective view of foam block 14. A bottom surface 38 of foam block 14 is positioned opposite work surface 21. At least a portion of bottom surface 38 may be angled to match an angle of sloping surface 30. As such, at least a portion of bottom surface 38 may be angled relative to work surface 21 and parallel to sloping surface 30. As can be seen in FIGS. 10 and 11, all portions of bottom surface 38 might be structured to match the angle of the corresponding surfaces of bottom side 29. In other embodiments, at least a portion of bottom surface 38 might not match the corresponding portion of bottom side 29 of fluid pan 12, however. For example, a part of bottom surface 38 may be substantially parallel with work surface 21 such that bottom surface 38 might not contact bottom side 29 at sloping surface 34. In such embodiments, a gap formed between bottom surface 38 and sloping surface 34 may allow fluids to pool in basin 32 prior to draining out of drainage outlet 16 such that tray 10 may be able to continue to drain fluids even if the rate at which the fluids are being spilled onto work surface 21 exceeds the rate at which the fluids are being drained out drainage outlet 16.

Referring now also to FIG. 12, a partially sectioned side view of tray 10 is shown. A perimeter 18 of foam block 14 might be heat-sealed or sealed by an adhesive, coating, or by any other suitable means such that perimeter 18 is fluid impermeable. In this way, foam block 14 can be positioned on top of fluid pan 12 without side 22, 24, 26, 28 of fluid pan 12 extending up to work surface 21. A top or layered section ("top section") 20 of foam block 14 may include one or more removable layers of the foam material. Each layer of the foam material can be attached to a lower layer by a relatively weak adhesive that allows layers to be removed during a procedure as they become contaminated. In other embodiments, an upper boundary of top section 20 may register with an upper boundary (not numbered) of sides 22, 24, 26, 28 before any layers of foam block 14 are removed, or foam block 14 might not include top section 20 at all.

As can also be seen, when foam block 14 is positioned on fluid pan 12, work surface 21 may be substantially parallel to horizontal plane 36. Further, at least a portion of bottom surface 38 may be in contact with the corresponding portion of bottom side 29. In other embodiments, one or more portions of bottom surface 38 might not contact the corresponding portions of bottom side 29 but instead be positioned close to bottom side 29. For example, in some embodiments, bottom surface 38 might be substantially parallel to but not contact bottom side 29 to allow fluids to flow on sloping surface 30 along flow path 25 without being obstructed by foam block 14.

Figure 13:
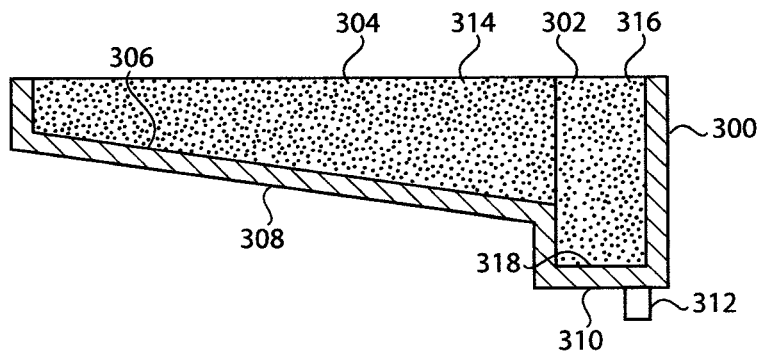
FIG. 13 is a sectioned side view of a drain tray assembly, according to one embodiment.

Referring to FIG. 13, a partially sectioned side view of a surgical drain tray assembly 300 for use during a medical procedure is shown. Drain tray/drain tray assembly 300 has a basin portion 310 and a sloped portion 308. Basin 310 includes a drainage outlet 312 which may be structured to couple drainage tubing (directly or using a fitting or adapter) with tray 300 for draining fluids from basin 310 during a procedure. A first foam block 302 having a work surface 316 is positioned in basin 310. First foam block 302 further includes a base surface 318 opposite work surface 316 and shaped to correspond and mate with basin 310. A second foam block 304 having a work surface 314 is positioned in sloped portion 308. Second foam block further includes a sloped surface 306 opposite work surface 314 and shaped to correspond to sloped surface 308. Optionally, foam blocks 302 and 304 may further include additional layers such as those described previously with respect to FIGS. 2-4, addition of any materials, such as anticoagulants, listed in connection with other embodiments, or any other features or functionality disclosed herein Referring to FIG. 14, a partially sectioned, exploded side view of a sterile packaging kit 320 for a drain tray 324 for use during a medical procedure. The sterile packaging kit 320 may include a storage tray 322 which is sized and configured so as to contain at least a surgical drain tray 324 and a foam block 328. Storage tray 322 may be made from metal, plastic, or other suitable material. Optionally, storage tray 322 is sized so as to contain additional items or materials as desired, such as a curtain or drape assembly 332 (shown here in a collapsed state) having, for instance a frame and/or an internal biaser 350, as well as a drainage fitting 330 for connecting a drainage outlet 326 on tray 324 to drainage tubing. Internal biaser 350 could be a rubber band, an elastic cord, a spring, or still another device that is attached directly or indirectly (such as to a frame) to a curtain or a drape herein, and can be elastically deformed against an internal bias to expand or adjust a curtain or drape, and imparting a tendency to return the curtain or drape to a collapsed state when a force opposing the bias is removed. Other items may also be included in storage tray 322 such as additional drainage fittings, drainage tubing, cords or straps, surgical instruments, and the like. A sealing film or envelope 334 seals items within storage tray 322 in a sterile environment until needed. In other embodiments, all the parts of the kit could be packaged in or on surgical drain tray 324, and storage tray 322 omitted from the design.

Figure 15:
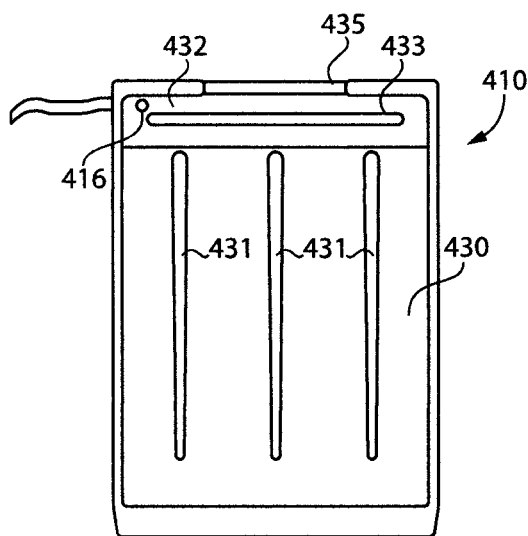
FIG. 15 is a top view of a drain tray, according to one embodiment.

Referring to FIG. 15, there is shown a drain tray 410 according to another embodiment. Drain tray 410 includes a sloping surface 430 for draining fluids to a basin 432, and thenceforth out a drain outlet 416. Drain tray 410 also includes an arcuate or other shaped cutout 435 that provides a relief in profile of the edge of drain tray 410 for accommodating a patient's limb. Drain tray 410 further includes a plurality of longitudinal or lengthwise ribs 431 that project upwardly from sloping surface 430, and generally increase in height relative to sloping surface 430 in a direction of basin 432. A widthwise rib 433 projects upwardly from a floor of basin 432, and basin 432 may slope toward drain outlet 416. Drain outlet 416 may be vertically oriented, extending down from basin 432 to join with a tube or fitting in a manner similar to foregoing embodiments. Alternatively drain outlet 416 could be horizontally oriented to enable connecting with a tube or fitting extending inwardly from a side of drain tray 410, for example. A number or size of ribs 431 and 433 could be varied to provide suitable fluid flow capabilities and/or to provide structural support and rigidity as desired to drain tray 410 or a foam block supported thereon. Drain tray 410 can be formed as a single piece of plastic, such as by thermoforming, injection molding, etc.

Figure 16:
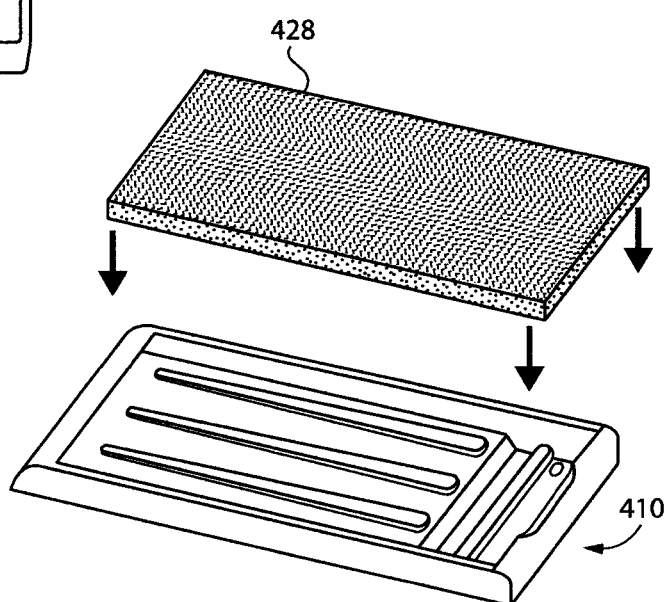
FIG. 16 is a perspective view of a drain tray assembly disassembled, according to one embodiment.
Figure 18:
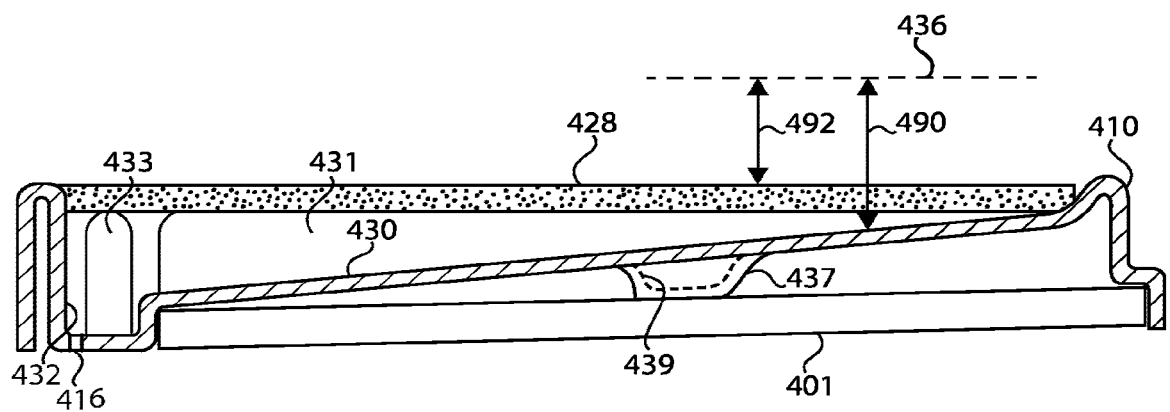
FIG. 18 is a sectioned side view of a drain tray assembly, according to one embodiment.

Referring also to FIG. 16, there is shown a foam block 428 as it might appear disassembled from drain tray 410. It can be noted foam block 428 has a generally uniform thickness, and can be cut from a sheet of foam, such as extruded or molded foam. Ribs 431 and 433 can thus be understood to project upwardly from sloping surface 430 and basin 432, respectively, and provide horizontal bottomside support for foam block 428. Referring also to FIG. 18, there is a shown a sectioned view through drain tray 410 and foam block 428 as they might appear positioned upon a table 401. It can be noted drain tray 410 may be situated so as to project over an edge of table 401 to enable facile connection of a tube or fitting to drain outlet 416. Providing ribs 431 can also be understood to enable fluid channels to be formed laterally between the respective ribs 431, and extending between an underside of foam block 428 and sloping surface 430. Also shown in FIG. 18 is a leg 437 that can extend downward to sit upon table 401. Leg 437 can provide additional structural support, and also may have a fluid cavity 439 formed therein that provides a collection volume for fluids that drain down through foam block 428. Also shown in FIG. 18 is a slope angle 490. Slope angle 490 is an angle formed between sloping surface 430 and a horizontal plane 436. Top work surface 428 is oriented at a work surface angle 492 relative to the horizontal plane. Work surface angle 492 is less than slope angle 490 and equal to 0° or greater. It will thus be understood from FIG. 18 that top work surface 428 can be substantially horizontal when drain tray 410 is positioned for service upon table 401. Embodiments are contemplated, however, where top work surface 428 dips slightly in a direction of basin 432 so as to have an inclination that assists in flow of fluids toward basin 416. In still other instances, embodiments according to the present disclosure could include a work surface angle that is equal to the slope angle. Accordingly, it will be understood that top work surface 428 may have an orientation, relative to horizontal plane 436, that ranges from parallel to horizontal plane 436 to parallel to sloping surface 430.

Figure 17:
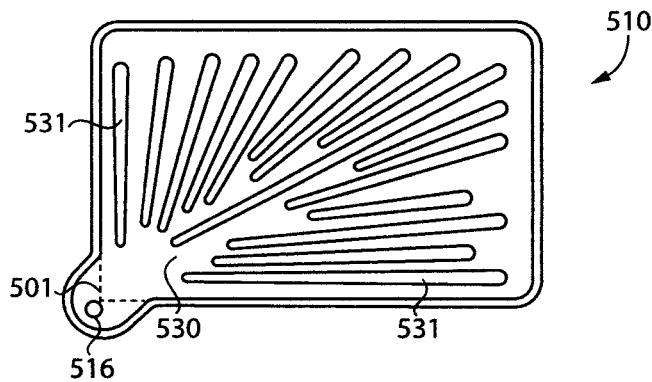
FIG. 17 is a top view of a drain tray, according to one embodiment.

Referring to FIG. 17, there is shown a top view of a drain tray 510 according to yet another embodiment. Drain tray 510 has certain similarities with previously described embodiments, but also certain differences. A sloping surface 530 extends generally toward a drain outlet 516. A plurality of ribs 531 extend upwardly from sloping surface 530 and have heights that vary generally inversely to the slope of sloping surface 530, and thus provide a plurality of generally horizontal support surfaces upon which a uniformly thick foam block can be positioned. It will thus be appreciated that fluid channels for fluids drained through the foam block will be formed between and among ribs 433, and along with ribs 433 themselves can be oriented so as be generally convergent with one another toward drain outlet 516. Also depicted in FIG. 17 in phantom is the corner of a table 501. It will be appreciated that drain tray 510 can be shaped so that drain outlet 516 can overhang the corner of table 501 for ease of attaching a tube, fitting, et cetera. Any other embodiments contemplated herein could include the overhanging drain outlet configuration and/or could be vertically oriented or horizontally oriented as discussed above with regard to drain tray 410.

Figure 19:
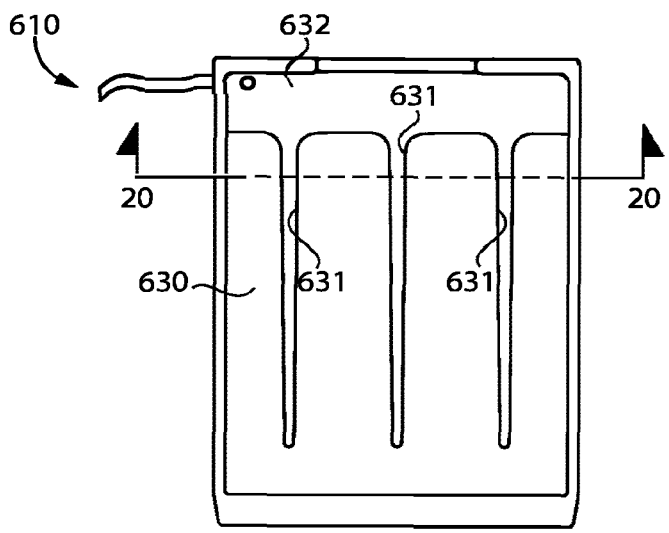
FIG. 19 is a top view of a drain tray, according to one embodiment.
Figure 20:
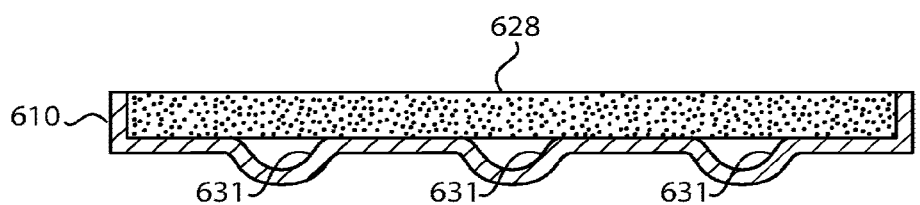
FIG. 20 is a sectioned view taken along line 20-20 of FIG. 19, according to one embodiment.

Referring now to FIGS. 19 and 20 there is shown a drain tray 610 according to yet another embodiment, and coupled with a foam block 628 in FIG. 20. Drain tray 610 has a sloping surface 630 that slopes to drain fluids toward and into a basin 632. A plurality of channels 631 may be molded into or otherwise formed in drain tray 410 so as to extend downwardly from sloping surface 630. In the side view of FIG. 20 it can be seen that foam block 628 is seated into contact with sloping surface 630, and that channels 631 form open fluid space below foam block 628 for draining fluids to basin 632. Foam block 628 could have a shape that mates with a shape of drain tray 610, similar to some of the foregoing embodiments such as in FIG. 13 or 14 and thus may not have a uniform thickness, but instead a varied thickness. As noted above, certain embodiments could utilize a foam block having channels formed therein, or including ribs, or potentially both a foam block having channels or ribs and a drain tray having channels or ribs formed therein.

Figure 21:
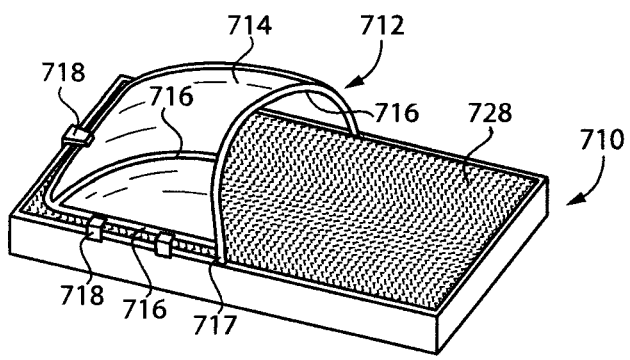
FIG. 21 is a diagrammatic view of a drain tray assembly, according to one embodiment.

Referring now to FIG. 21, there is shown a drain tray 710 in combination with a foam block 728 and a drape assembly 712 to form a drain tray assembly. The features and functions of drain tray 710 itself and foam block 728 could be similar to any of the other embodiments contemplated herein, thus drain tray could include channels or ribs, for instance, and foam block 728 could have a uniform thickness or a varying thickness, for instance, or comprise multiple pieces. Each of the embodiments herein may include cooperating structure(s) of a drain tray and a foam block that enable the drain tray to be sloped for draining fluid, and the foam block to provide a horizontal top work surface, or potentially a top work surface that dips toward a fluid collection basin in an associated tray. Drape assembly 712 may include a drape 714 and a frame 716 for drape 714. Drape 714 could be formed of clear or translucent, thin plastic sheeting or film, for instance, or could be formed from opaque or translucent cloth or any other suitable flexible material. Frame 716 can include a plurality of relatively thin elongate frame elements, generally having the form of rods, that assist in providing shape to drape 714, such as a generally half-dome shape as shown. Each of frame 716 and drape 714 can be collapsed down for packaging, or during use, and then reassume or approximate an original intended shape. In other words, frame 716 can have sufficient elastic and/or shape memory properties that even when drape assembly 712 is flattened against foam block 728, such as for storage or packaging, drape assembly 712 can be easily returned to an original shape or approximating an original shape. Frame 716 could include plastic or metallic elongate rod pieces that are attached to, or attached close to, outer edges of drape 714, approximately as shown, as well as including some internal elongate rod pieces providing one or more backbone structures to drape assembly 712.

Also shown in FIG. 21 are a plurality of fastener clips 718 that can be used to secure drape assembly 712 to one or both of drain tray 710 and foam block 728. In one practical implementation strategy, fastener clips 718 can be adjusted between a release state and a clipped state attached to drain tray 710. Fastener clips 718 could be irreversibly attached to drape assembly 712, or irreversibly attached to drain tray 710. Providing fastener clips 718 that can be adjusted in this manner can enable drape assembly 712 to be adjusted to different locations, or removed and set aside if it is not desirable to use drape assembly 712 for a particular procedure. It will generally be desirable for drape assembly 712 to be attached to an inside of drain tray 710 to assist in forming a watertight or substantially watertight seal, such that fluids from aggressive irrigation will remain contained and drain down through the foam.

Figure 22:
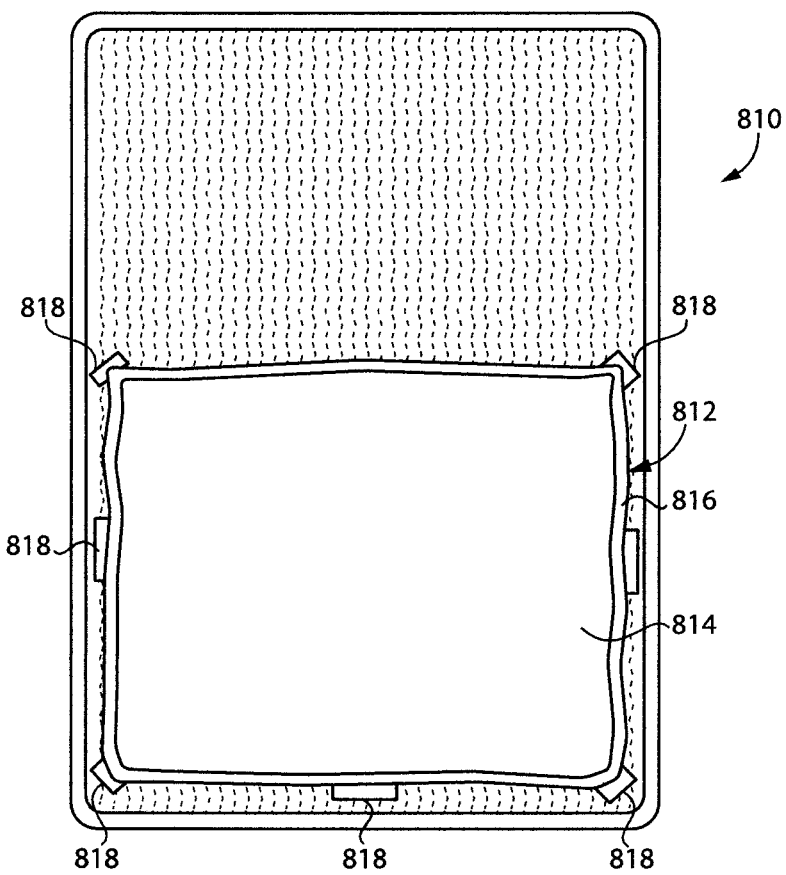
FIG. 22 is a top view of a drain tray assembly, according to one embodiment.

Referring now to FIG. 22, there is shown a drain tray 810 in an assembly with a foam block and drape assembly 812. Drape assembly 812 includes a drape 814 and frame 816 generally similar to the embodiment of FIG. 21. Drape assembly 812 differs from drape assembly 712, however, in that drape assembly 812 includes a plurality of fasteners that attach directly to the foam block. One implementation includes fasteners similar to Velcro® having hooks that can releasably engage directly with the foam surface. Other fastener arrangements could include metallic pins or hooks, for instance, that could pierce the foam to attach drape assembly 812. In any of the embodiments contemplated herein, the drape in the drape assembly could include holes or ports for the patient's limb, or for tubes or the like. It is contemplated that a physician could rearrange the location of a drape assembly during a procedure, for instance, where work on one part of a patient's limb is completed or paused, and work on another part of a patient's limb commenced.

To this end, FIG. 23 illustrates a sectioned view of one arrangement where a drape assembly 912 is releasably attached, and movable relative, to a drain tray 910. Drape assembly 912 includes a drape 914 and a frame 916. Frame 916 may be equipped with a channel 919 that fits over and onto a side wall of drain tray 910. Drape assembly 912 could rest quiescently upon drain tray 410 in some embodiments, or an interference fit of frame 916 upon drain tray 910 could be provided, such that the side wall of drain tray 910 snaps into engagement in channel 919. In another embodiment, a channel similar to channel 919 might be formed in the exposed top edge of drain tray 910, and an elongate rod piece of drape assembly 912 received therein. FIG. 24 illustrates another arrangement for coupling a drape assembly 1012 to a drain tray 1010, and provides a channel 1019 formed in the side of a sidewall of drain tray 1010. A drape assembly 912 includes a drape 1014 and a frame 1016, with frame 1016 interference-fitted into channel 1019. Once snapped into engagement within channel 1019, drape assembly 1012 could be slid relatively freely relative to drain tray 1010, in and out of the page in the FIG. 24 illustration. FIG. 25 illustrates yet another arrangement for coupling a drape assembly 1112 having a drape 1114 with a drain tray 1110.

In FIG. 25, drain tray 1110 forms a track 1119 and a frame 1116 of drape assembly 1112 is shaped as a track follower that is mated with track 1119. Drape assembly 1112 can be slid along track 1119, in and out of the page in the FIG. 25 illustration, to any selected position upon drain tray 1110. In any of the embodiments of FIGS. 23-25, each longitudinal side of the respective drain tray can be coupled with the respective drape assembly according to the illustrated arrangement.

Referring now to the drawings generally, systems for draining fluids such as blood, irrigant, or other fluids during a medical procedure are illustrated. The following description can be understood to apply by analogy to any of the embodiments contemplated herein. Fluids spilled out or otherwise flowing from a working site during a medical procedure on to work surface 21 may pass through foam block 14 under the force of gravity toward sloping surface 30. Particles within the fluid that have a dimension equal to or larger than a dimension of the pores of the foam material may come to rest on work surface 21. The fluids may then contact sloping surface 30 and be conveyed along flow path 25 toward basin 32. It will be appreciated that some fluids passing through foam block 14 may not contact sloping surface 30 but instead may be influenced by sloping surface 30 to flow along flow path 25 within foam block 25 toward basin 32. Upon reaching basin 32, the fluids may then contact sloping surface 34 or otherwise be influenced by sloping surface 34 to flow along flow path 27 toward drainage outlet 16. Drainage tubing (not pictured) attached to connector piece 23 may couple drainage outlet 16 with a fluid collection and/or suction device (not shown) suitable for use in the medical context, for example, a Neptune™ collection chamber device or any other similar device or wall suction that may be commercially or readily available in the operating room, clinic or emergency room setting. The fluid collection device may generate suction to draw fluids from basin 32. It will be appreciated that using foam block 14 to create work surface 21 may allow for the vacuum created by this type of fluid collection device to be at least partially maintained adjacent to drainage opening 16. As such, the fluid draining system discussed herein may be able to use a wider array of fluid collection devices than other drainage strategies. In other embodiments, fluids may be drawn out of tray 10 under the force of gravity alone or by any other suitable means such as for example a collection bag, bottle, or basin.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure. For instance, tray 10 could be equipped with one or more peel-away coverings that could be selectively removed during use, such as where tray 10 is used without foam block 14. It will be appreciated that certain features and/or properties of the present disclosure, such as relative dimensions or angles, may not be shown to scale. As noted above, the teachings set forth herein are applicable to a variety of different assemblies, devices, systems, and methods having or employing a variety of different structures than those specifically described herein. Discussion herein of features or functionality of any one embodiment may be understood by way of analogy to refer to any other embodiment except where otherwise indicated or apparent from the context. Other aspects, features, and advantages will be apparent upon an examination of the attached drawings and appended claims. As used herein, the articles "a" and "an" are intended to include one or more items, and may be used interchangeably with "at least one." Where only one item is intended, the term "one" or similar language is used. Also, as used herein, the terms "has," "have," "having," or the like are intended to be open-ended terms.

What is claimed is:

1. A drain tray assembly for use during a medical procedure comprising:
a fluid impermeable pan layer including a basin, a first sloping surface angled toward the basin so as to direct a flow of fluids, upon the fluid impermeable pan layer, toward the basin in a first flow path and oriented at a slope angle relative to a horizontal plane;
a drainage outlet within the basin;
the basin including a second sloping surface angled toward the drainage outlet so as to direct a flow of fluids, upon the fluid impermeable pan layer and within the basin, toward the drainage outlet in a second flow path transverse to the first flow path; and
the fluid impermeable pan layer further including an edge formed between the first sloping surface and the basin and oriented transverse to the first flow path.

2. The drain tray assembly of claim 1 further including a drape assembly having a drape, an elastically deformable frame supporting the drape, and a plurality of fasteners releasably attaching the drape assembly to the fluid impermeable pan layer.

3. The drain tray assembly of claim 1 wherein the fluid impermeable pan layer includes a plurality of upwardly projecting ribs, such that channels are formed along the sloping surface in the direction of the basin.

4. The drain tray assembly of claim 1 wherein the fluid impermeable pan layer is within a sealed, sterile storage envelope.

5. The drain tray assembly of claim 4 wherein a drape assembly is within the sealed, sterile storage envelope.

6. The drain tray of claim 1, further comprising at least one fluid cavity formed in the first sloping surface to collect fluids.

7. The drain tray of claim 1, the fluid impermeable pan layer further includes a first side wall having an arcuate cut out.

8. The drain tray of claim 7, wherein the first side wall is proximal to the basin.

9. The drain tray of claim 7, wherein the first side wall is distal to the basin.

10. A system for draining fluids during a medical procedure comprising:
a drain tray assembly including a fluid impermeable one-piece pan having a sloping surface bounded by a first sidewall, a second sidewall, a third sidewall, and a fourth sidewall, the second sidewall transverse to the first sidewall to form a corner, and a drain outlet located adjacent to the corner formed by the first sidewall and the second sidewall;
a suction tube device positioned at the corner for drawing fluids from the drain outlet; and
the sloping surface of the fluid impermeable pan being convergent towards the corner so as to direct fluids only to the corner formed by the first and second sidewalls under the force of gravity.

11. The system of claim 10 further comprising a drape assembly coupled with the drain tray assembly.

12. The system of claim 10 further comprising a fluid collection device coupled with the drain outlet.

13. The system of claim 10 wherein the fluid impermeable one-piece pan of the drain tray assembly has a plurality of channels formed therein that are convergent towards the drain outlet.

14. The system of claim 10 wherein the second side wall has an arcuate cut out portion for accommodating a patient's limb.

15. The system of claim 10 wherein the third sidewall is transverse to the first sidewall and has an arcuate cut out for accommodating a patient's limb.

16. The system of claim 10 wherein the fluid impermeable pan layer includes a plurality of upwardly projecting ribs, such that channels are formed along the sloping surface in the direction of the drain outlet.

17. A method of draining fluids during a medical procedure comprising:
receiving fluids on a sloping work surface bounded by a first sidewall, a second sidewall, a third sidewall, and a fourth sidewall and formed on a layer of a fluid impermeable material of a drain tray of a drain tray assembly, the second sidewall transverse to the first sidewall to form a corner, and the sloping work surface being convergent towards the corner formed by the first and second sidewalls;
conveying the fluids under the force of gravity only toward the corner formed by the first sidewall and the second sidewall; and
drawing the fluids from the drain tray by way of a suction device at the corner of the drain tray.

18. The method of claim 17 wherein a drainage outlet comprising an opening in the sloping work surface is located adjacent to the corner.

19. The method of claim 17 further comprising supporting a limb of a patient upon the work surface.

20. The method of claim 19, further comprising accommodating the patient's limb in an arcuate cutout formed in the first side wall of the one-piece drain tray of a drain tray assembly.

* * * * *